United States Patent [19]
Jackson et al.

[11] Patent Number: 4,888,041
[45] Date of Patent: Dec. 19, 1989

[54] GRAIN SELECTIVE HERBICIDES

[75] Inventors: Lucinda A. Jackson, Pleasant Hill; Sudarshan K. Malhotra, Walnut Creek, both of Calif.

[73] Assignee: The Dow Chemical Company, Midland, Mich.

[21] Appl. No.: 51,442

[22] Filed: May 18, 1987

[51] Int. Cl.$^4$ ...................... A01N 43/80; A01N 43/40
[52] U.S. Cl. ........................................... 71/88; 71/94; 546/270
[58] Field of Search ...................................... 71/88, 94

[56] References Cited

U.S. PATENT DOCUMENTS 4,571,255  2/1986  Nielsen ................................... 71/88

*Primary Examiner*—Catherine L. Mills
*Attorney, Agent, or Firm*—D. Wendell Osborne

[57] ABSTRACT

Certain 5-(substituted phenoxy and substituted 2-pyridinyloxy)-3-methylbenzisoxazoles are selective herbicides for use in grain crops. The control of weeds in rice by the post-emergence application of 5-(2-chloro-4-(trifluoromethyl)phenoxy)-3-methylbenzisoxazole is exemplary. The pyridinyloxy substituted compounds are novel.

9 Claims, No Drawings

GRAIN SELECTIVE HERBICIDES

BACKGROUND OF THE INVENTION

The ability of modern agriculture to produce abundant supplies of food and fiber at low cost is highly dependent on the existence of means to selectively control weeds in the presence of crop plants. While chemicals which have this capability are known, new compounds that can be used in smaller amounts, that more effectively control specific problem weeds, that cause less damage to the crop, that are less toxic, or that have other desirable characteristics are desirable.

Certain phenoxybenzoxazoles, such as 5-(2-chloro-4-(trifluoromethyl)phenoxy)-3-methylbenzisoxazole, are disclosed to be effective in the control of many broadleaf and grassy weeds in U.S. Pat. No. 4,571,255, the teachings of which are hereby incorporated by reference.

SUMMARY OF THE INVENTION

It has now been found that certain 5-(substituted phenoxy or substituted 2-pyridinyloxy)-3-methylbenzisoxazoles are of relatively low toxicity to valuable grain producing plants and can be used to selectively control weeds in grain crops. The novel method for selectively controlling weeds in the presence of a grain crop comprises applying to the locus of the crop a selectively effective amount of a compound of the formula

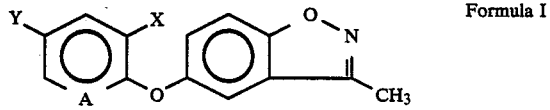

Formula I wherein
A represents CH or N;
X represents H, F, Cl, or Br; and
Y represents F, Cl, Br, CF$_3$, or CN.

The application can be made either before or after emergence of the crop and is effective for the selective control of many species of both broadleaf and grassy weeds. Rice crops are particularly suited and rice grown using either dry-land or paddy cultural practices can be treated. 5-(2-Chloro-4-(trifluoromethyl)phenoxy)-3-methylbenzisoxazole is a preferred compound.

Compounds of Formula I wherein A represents N are novel and these compounds are another aspect of the present invention.

DETAILED DESCRIPTION OF THE INVENTION

The 5-(substituted phenoxy or substituted 2-pyridinyloxy)-3-methylbenzisoxazole compounds found to be useful in the selective control of weeds in grain crops are given by Formula I wherein A, X, and Y are defined as in the Summary of the Invention. Compounds wherein A represents CH are preferred as are compounds wherein Y represents CF$_3$. The compound 5-(2-chloro-4-(trifluoromethyl)phenoxy)-3-methylbenzisoxazole is especially preferred.

The compounds of Formula I can be prepared by the methods described in U.S. Pat. No. 4,571,255, which descriptions are hereby incorporated by reference, or by simple adaptations thereof. Thus, in a first process, an appropriate 5-(substituted phenoxy or substituted 2-pyridinyloxy)-2-nitroacetophenone oxime can be cyclized with a base or, alternatively, in a second process, an appropriate substituted fluorobenzene or substituted 2-halopyridine can be condensed with 5-hydroxy-3-methylbenzisoxazole in the presence of a base. The starting materials required for the first process and methods for their preparation are generally known from U.S. Pat. Nos. 4,344,789 and 4,539,039; those required for the second process are well known in the art.

The following examples are presented to further illustrate the preparative procedures.

EXAMPLE 1

Preparation of 5-(2-fluoro-4-bromophenoxy)-3-methylbenzisoxazole

The starting material 1-(5-(2-fluoro-4-bromophenoxy)-2-nitrophenyl)ethanone oxime was prepared from 2-fluoro-4-bromophenol and 5-chloro-2-nitroacetophenone by combining 4.0 g of each with 3.0 g of potassium carbonate in 50 ml of dimethyl sulfoxide and heating at about 100° C. for about two hours. The resulting mixture was cooled, diluted with water, and extracted with ether. The ether extract was washed with water, dried over magnesium sulfate, and concentrated by evaporation to obtain a viscous oil. This was triturated with a mixture of ether and hexane and recrystallized from methanol to obtain about 3.2 g of 5-(2-fluoro-4-bromophenoxy)-2-nitroacetophenone; m.p., 116°–117° C. Elemental (CHN) and nmr analyses consistent with the assigned structure were obtained.

A 10.0 g (0.028 mol) sample of the above product, 4.0 g (0.050 mol) of hydroxylamine hydrochloride, and 6.0 g of triethylamine were combined with 50 ml of benzene and 150 ml of absolute ethanol and the mixture heated to reflux for 15 minutes. About 100 ml of solvent was removed by distillation and replaced by 75 ml of benzene. After refluxing another 0.5 hour, another 75 ml of solvent was removed by distillation. The resulting mixture was heated at reflux for about 16 hours, cooled, diluted with water, and extracted with ether. The ether extract was washed with water, dried over magnesium sulfate, and concentrated by evaporation to obtain 10.2 g of the oxime as a viscous brown oil. This appeared to be about half syn and half anti isomer of the desired 1-(5-(2-fluoro-4-bromophenoxy)phenylethanone oxime.

A 2.0 g sample of the oxime prepared as above was combined with 1.2 g of potassium carbonate in 25 ml of dimethyl sulfoxide and the mixture was allowed to stir at room temperature for two days. The resulting mixture was diluted with water and extracted with ether. The ether extract was washed with water, dried over magnesium sulfate, and concentrated under reduced pressure. The resulting oil was distilled in a Kugelrohr apparatus to obtain 0.6 g of a thick, amber oil, the nmr spectrum of which was consistent with the assigned structure.

Analysis: Calc. for C$_{14}$H$_9$BrFNO$_2$: C, 52.2%; H, 2.80%; N, 4.35% Found: C, 52.1%; H, 3.03%; N, 4.79%.

EXAMPLE 2

Preparation of 5-(3-fluoro-5-(trifluoromethyl)-2-pyridinyloxy)-3-methylbenzisoxazole A mixture of about 4 g of impure 1-(5-(3-fluoro-5-(trifluoromethyl)-2-pyridinyloxy)phenyl)ethanone oxime and 2 g of potassium carbonate in dimethyl sulfoxide was heated at about 100° C. for about one hour. The resulting mixture was cooled, diluted with water, and extracted with ether. The ether extract was washed with water, dried over magnesium sulfate, and concentrated by evaporation of the solvent to obtain a yellow oil. This was distilled in a Kugelrohr apparatus at 180°–190° C. and 1 mmHg pressure to obtain about 0.5 g of the product as a yellow oil. The nmr spectrum of this was compatible with the assigned structure.

Analysis: Calc. for $C_{14}H_8F_4N_2O_2$: C, 53.9%; H, 2.56%; N, 8.97%; Found: C, 52.1%; H, 2.53%; N, 9.00%. The following were prepared in a similar manner: 5-(2,4-dichlorophenoxy)-3-methylbenzisoxazole: (thick, light brown oil).

Analysis: Calc. for $C_{14}H_9Cl_2NO_2$: C, 57.1%; H, 3.01%; N, 4.76% Found: C, 56.7%; H, 3.49%; N, 4.76%. 5-(2-chloro-4-(trifluoromethyl)phenoxy)-3-methylbenzisoxazole: (light yellow oil after distillation in a Kugelrohr apparatus at 170°–190° C. and 15–20 mmHg pressure).

Analysis: Calc. for $C_{15}H_9ClF_3NO_2$: C, 55.0%; H, 2.75%; N, 4.27% Found: C, 55.0%; H, 2.78%, N, 4.27%.

While it is possible to utilize the benzisoxazole compounds of Formula I directly as selective herbicides, it is preferable to use them in mixtures containing an herbicidally effective amount of the compound along with at least one agriculturally acceptable adjuvant or carrier. Suitable adjuvants or carriers should not be phytotoxic to grain crops, particularly at the concentrations employed in applying the compositions for selective weed control in the presence of grain crops, and should not react chemically with the compounds of Formula I or other composition ingredients. Such mixtures can be designed for application without dilution to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether, diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenolalkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorants, penetration aids, spreading agents, sticking agents, dispersing agents, thickening agents, freeze point depressants, antimicrobial agents, and the like. The compositions can also contain other compatible components, for example, other grain selective herbicides, plant growth regulants, fungicides, insecticides, and the like and can be formulated with solid, particular fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters and sprayers, by addition to flood or irrigation water, and by other conventional means known to those skilled in the art.

The compounds of Formula I have been found to be selective herbicides useful in controlling many species of weed plants in grain crops with acceptably minor damage to the crop. This selective herbicidal property is exhibited in both pre- and post-emergence applications. Applications made after the emergence of the crop, which may be before or after emergence of the weeds, are preferred.

The grain crops of the present invention are purposefully grown cereal grasses and include corn, wheat, barley, and rice. Rice is a preferred grain crop. The method is useful for both indica varieties, such as starbonnet, and japonica varieties, such as S-201, and for rice grown in a variety of cultural methods including paddy and dry land methods.

The weed species controlled include examples of both broadleaf and grass type plants. Among the broadleaf weeds controlled are morning glory, smartweed, jimsonweed, velvet leaf, coffeeweed, pigweed, and arrowhead. Grassy weeds controlled include barnyard grass, yellow foxtail, and sprangletop.

As will be appreciated by those skilled in the art, not all of the compounds control all of the weeds or are selective when applied at all rates or in every conceivable way to grain crops grown under every conceivable culture. Suitable procedures are, however, readily ascertained using the information presented.

The term "herbicide" is used herein to designate an active ingredient which controls or adversely modifies the growth of plants. By "growth controlling" or "herthe plants were maintained in a greenhouse under conditions conducive to plant growth. Two weeks after treatment the plants were examined for growth and evaluated on a scale of 0 to 100 where 0 represents no effect and 100 represents complete kill. In this test 100 ppm represents about 0.25 Kg/Ha. The compounds and plant species tested, the application rates employed, and the representative results obtained in this test are given in the following table.

POST-EMERGENCE HERBICIDAL ACTIVITY OF COMPOUNDS OF FORMULA I

| #A | #X | #Y | RATE, PPM | JIMSON-WEED | MORNING GLORY | PIG-WEED | VEL-VET LEAF | BARN-YARD GRASS | CRAB-GRASS | YEL-LOW FOX-TAIL | CORN | RICE | WHEAT |
|----|----|----|-----------|-------------|---------------|----------|--------------|-----------------|------------|------------------|------|------|-------|
| CH | Cl | CF$_3$ | 250 | 100 | 100 | 100 | 100 | 100 | 100 | 100 | 70 | 0 | 0 |
|    |    |    | 125 | 100 | 100 | *NT | *NT | 80 | 100 | 100 | 0 | 0 | 0 |
| CH | Cl | Cl | 250 | 98 | 0 | 100 | 100 | 0 | 0 | 20 | 0 | 0 | 0 |
| CH | F  | Br | 250 | 0 | 0 | 100 | 100 | 0 | 0 | 100 | 0 | 0 | 0 |
| N  | F  | CF$_3$ | 250 | 50 | 50 | 100 | 80 | 0 | 50 | 0 | 0 | 0 | 0 | refers to substituents on Formula I
*NT means "no test"

bicidally effective" amount is meant an amount of active ingredient which causes an adversely modifying effect and includes deviations from natural development, killing, regulation, dessication, retardation, and the like. A "selectively effective amount" is an amount which is herbicidally effective to weeds, but causes little or no damage to the specified crop. The terms "plants" and "weeds" are meant to include germinant seeds, emerging seedlings, and established vegetation.

Herbicidal activity is exhibited by the compounds of the present invention when they are applied directly to the weed or to the locus of the weed, at any stage of growth or before emergence. The effect observed depends upon the weed species to be controlled, the stage of growth of the weed, the application parameters of dilution and spray drop size, the particle size of solid components, the environmental conditions at the time of the test, the specific compound employed, the specific adjuvants and carriers employed, and the like, as well as the amount of chemical applied. These and other factors can be adjusted as is known in the art to promote selective herbicidal action.

Application rates of about 0.01 to about 10 Kg/Ha are generally employed in post-emergence operations; for pre-emergence applications, rates of about 0.02 to about 20 Kg/Ha are generally employed. The preferred rates are about 0.1 to about 5 and about 0.2 to about 5 Kg/Ha, respectively.

The following utility examples are illustrative of the herbicidal activity exhibited by compounds of Formula I.

EXAMPLE 3

Evaluation of Post-Emergence Herbicidal Activity

Representative compounds of Formula I were evaluated for the post-emergence control of a variety of species of plants. In these evaluations the test plants were grown to a height of about four inches and were then sprayed to run-off with aqueous compositions containing known concentrations of the compounds using conventional spray equipment. The spray compositions were prepared by mixing the required amount of active ingredient and an emulsifier or dispersant in an aqueous acetone carrier to form an emulsion or suspension. Control plants were sprayed in the same manner with like compositions omitting the active ingredient. Thereafter,

EXAMPLE 4

Post-Emergence Activity in Paddy Rice

Rice Plants and weeds were grown in soil in 5-cm-diameter pots until the plants were in the 1 to 3 leaf stage (1 to 3 weeks depending on the species). They were then transplanted into 10-cm-diameter cottage cheese containers containing a sandy soil. The pots were flooded to approximately 2.5 cm depth of water and the plants allowed to acclimate for 24 hours prior to treatment. For the overall spray treatment the water level was lowered as needed so that the plant leaves were exposed. The test compound was applied with a hand syringe spray device at various known concentrations in a 50:50 mixture of acetone and a 0.1 percent solution of Ortho X-77 surfactant. For the flood water treatment the water level was adjusted as needed so the weeds were immersed but the rice was still exposed. Various known amounts of test compound in acetone solution were applied by means of a needle syringe into the paddy water to achieve known rates of application. In both cases evaluations were made two weeks after treatment on a linear scale with 0 representing no effect and 100 representing complete kill. Some of the dosages applied and results obtained for 5-(2-chloro-4-(trifluoromethyl)phenoxy)-3-methylbenzisoxazole are given in the following table.

POST-EMERGENCE CONTROL OF WEEDS IN PADDY RICE WITH 5-(2-CHLORO-4-(TRIFLUOROMETHYL)-PHENOXY-3-METHYLBENZISOXAZOLE

| WEEDS/CROPS | FLOOD WATER TREATMENT | | OVERALL SPRAY TREATMENT |
|-------------|-------------|-------------|------------|
|             | 2 lb/A | 0.25 lb/A | 125 ppm |
| Barnyard Grass | 100 | 95 | 70 |
| Sprangletop | 100 | 80 | 100 |
| Morning Glory | 90 | 100 | 85 |
| Smartweed | 100 | 50 | 100 |
| Coffeeweed | 85 | 15 | 100 |
| Arrowhead | 75 | 40 | 10 |
| Hardstem Bulrush | 90 | 30 | 0 |

| | FLOOD WATER TREATMENT | | OVERALL SPRAY TREATMENT |
|---|---|---|---|
| WEEDS/CROPS | 2 lb/A | 0.25 lb/A | 125 ppm |
| Rice | 0 | 0 | 20 |

EXAMPLE 5

Evaluation of Pre-Emergence Herbicidal Activity 5-(2-chloro-4-(trifluoromethyl)phenoxy)-3-methyl-benzisoxazole was evaluated for the pre-emergence control of a variety of species of plants. In these evaluations, seeds were planted in pots in an agricultural soil and immediately thereafter measured quantities of the test chemical were drenched onto the soil surface as an aqueous emulsion or suspension and allowed to leach into the soil. The aqueous emulsions or suspensions were prepared by mixing the required amount of active ingredient in an aqueous acetone carrier containing 0.1 percent by weight surface-active agent. Control pots were drenched with a like mixture omitting the active ingredient. The pots were maintained in a greenhouse under conditions conducive to germination and growth. About two weeks after treatment the test was graded on a scale of 0–100 where 0 represents no effect and 100 represents complete kill. At the 2 lb/A dose rate barnyard grass, yellow foxtail, jimsonweed, and velvet leaf all had scores of 100 while Johnsongrass scored 70 and morning glory 50. Rice was damaged only to the extent of a 5 score at this rate.

What is claimed is:

1. A method for selectively controlling weeds in the presence of a grain crop which comprises applying to the locus of the emerged crop a selectively effective amount of a compound of the formula

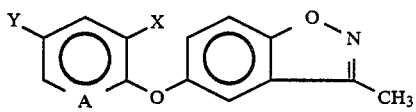

wherein
A represents CH or N;
X represents H, F, Cl, or Br; and
Y represents F, Cl, Br, CF$_3$, or CN.

2. A method of claim 1 wherein A represents CH.
3. A method of claim 1 wherein Y represents CF$_3$.
4. A method of claim 3 wherein A represents CH.
5. A method of claim 4 wherein X represents Cl.
6. A method of claim 1 wherein the crop is rice.
7. A method of claim 5 wherein the crop is rice.
8. A method of claim 6 wherein the rice crop is grown in a dry land cultural method.
9. A method of claim 6 wherein the rice crop is grown in a paddy cultural method.

* * * * *